United States Patent [19]
Baker et al.

[11] Patent Number: 5,073,557
[45] Date of Patent: Dec. 17, 1991

[54] NOVEL SUBSTITUTED PYRAZINE, FORMULATIONS THEREOF AND USE IN MEDICINE

[75] Inventors: Raymond Baker, Much Hadham; Leslie J. Street, Harlow; John Saunders, Amwell Grange, all of England

[73] Assignee: Merck Sharp & Dohme Limited, Hertfordshire, England

[21] Appl. No.: 564,490

[22] Filed: Aug. 8, 1990

[30] Foreign Application Priority Data

Aug. 8, 1989 [GB] United Kingdom ................ 8918060

[51] Int. Cl.$^5$ ........................................... C07D 453/02
[52] U.S. Cl. ................................... 514/254; 544/409; 544/336
[58] Field of Search ................ 514/254; 544/409, 336

[56] References Cited

U.S. PATENT DOCUMENTS 4,442,096  4/1984  Johnston .................. 544/109 X
4,970,315  11/1990  Schmidhalter ............. 544/109 X

FOREIGN PATENT DOCUMENTS 200147  11/1986  European Pat. Off. .
239309   3/1987  European Pat. Off. .
327155   1/1989  European Pat. Off. .

OTHER PUBLICATIONS

CAS (Chemical Abstracts Service) vol. 112, 1990, 112:77224q.

Primary Examiner—Catherine S. Kilby Scalzo
Attorney, Agent, or Firm—Manfred Polk; Charles M. Caruso

[57] ABSTRACT

The compound (R)-3-[2-(6-chloropyrazin)yl]-1-azabicyclo[2.2.2]octane and its salts behave as $M_1$, $M_3$ muscarinic agonists and are useful in the treatment of neurological and mental disorders, preferably in a pharmaceutical formulation comprising the active compound in association with a pharmaceutically acceptable carrier. The compound can be prepared by via methods analogous to those known in the art and a chiral acid resolution.

6 Claims, No Drawings

NOVEL SUBSTITUTED PYRAZINE, FORMULATIONS THEREOF AND USE IN MEDICINE

The present invention relates to a substituted pyrazine compound which stimulates central muscarinic acetylcholine receptors and therefore is useful in the treatment of neurological and mental illnesses whose clinical manifestations are due to cholinergic deficiency. Such diseases include presenile and senile dementia (also known as Alzheimer's disease and senile dementia of the Alzheimer type respectively), Huntington's chorea, tardive dyskinesia, hyperkinesia, mania and Tourette syndrome. Alzheimer's disease, the most common dementing illness, is a slowly progressive neurological disorder characterised by marked deficits in cognitive functions including memory, attention, language and visual perception capabilities.

European Patent Application No. 89200147 (Publication No. 327155) discloses a class of pyrazines, pyridazines or pyrimidines, and salts and prodrugs thereof, substituted on one of the ring carbon atoms thereof with a non-aromatic azacyclic or azabicyclic ring system; and independently substituted on each of the other ring carbon atoms with a substituent of low lipophilicity or a hydrocarbon substituent, which compounds stimulate cholinergic transmission. It has now been found that a single optical isomer of one of the racemates of this class exhibits $M_1$ and $M_3$ agonist activity (as measured in the ganglion and ileum, respectively) and $M_2$ antagonist activity (as measured in the heart).

Thus, the present invention provides (R)-3-[2-(6-chloropyrazin)yl]-1-azabicyclo[2.2.2]octane and salts thereof (hereinafter collectively referred to as compound (I)). Surprisingly, it has been found that compound (I) exhibits twice the potency of the corresponding racemate and four times that of the corresponding (S)-enantiomer at the $M_1$ receptor, as shown in the biological activity examples hereinbelow.

Also included within the scope of the present invention are salts of (R)-3-[2-(6-chloropyrazin)yl]-1-azabicyclo[2.2.2]octane. It will be appreciated that salts of the compound for use in medicine will be non-toxic pharmaceutically acceptable salts. Other salts may, however, be useful for the preparation of the base or its non-toxic pharmaceutically acceptable salts. Acid addition salts, for example, may be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid, p-toluene sulphonic acid or phosphoric acid. Preferred are the hydrochloride, hydrogen maleate, sesquioxalate and hydrogen tartrate salts, especially the hydrogen tartrate.

This invention also provides a method of treating Alzheimer's disease, senile dementia of the Alzheimer type, Huntington's chorea, tardive dyskinesia, hyperkinesia, mania or Tourette syndrome by the administration to a patient in need of such treatment of a pharmacologically effective amount of compound (I).

It may, where appropriate, be advantageous, in order to reduce unwanted peripherally mediated side-effects, to incorporate into the composition a peripherally acting cholinergic antagonist (or anti-muscarinic agent). Thus compound (I) may be administered together with a peripheral cholinergic antagonist such as methantheline or glycopyrrolate.

Compound (I) can be administered orally, parenterally or rectally at a daily dose of about 0.01 to 10 mg/kg of body weight, preferably about 0.1 to 1 mg/kg, and may be administered on a regimen of 1–4 times a day. When a cholinergic antagonist is administered, it is incorporated at its conventional dose.

This invention also provides a pharmaceutical composition comprising compound (I) and a pharmaceutically acceptable carrier therefor.

The pharmaceutical formulations of this invention preferably are in unit dosage form such as tablets, pills, capsules, powders, granules, sterile parenteral solutions or suspensions, or suppositories which forms are for oral, parenteral or rectal administration. For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of compound (I). When referring to these preformulation compositions as homogeneous, it is meant that the active ingredient is dispersed evenly throughout the composition so that the composition may be readily subdivided into equally effective unit dosage forms such as tablets, pills or capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups and flavoured emulsions with edible oils such as cottonseed oil, sesame oil, coconut oil and peanut oil, as well as elixirs and similar pharmaceutical vehicles. Suitable dispersing or suspending agents for aqueous suspension include synthetic and natural gums such as tragacanth, acacia, alginate, dextran, sodium carboxymethylcellulose, methylcellulose, polyvinylpyrrolidone and gelatin.

The present invention therefore further provides a process for preparing a pharmaceutical composition according to the invention which process comprises bringing compound (I) into association with a carrier therefor, such as by mixing.

Compound (I) may be prepared by a process which comprises the dehydroxylation or decarboxylation of a compound of formula (III) or a salt thereof:

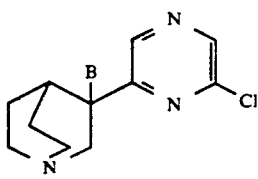

wherein B represents hydroxy or a carboxy-containing group such as the residue of a carboxylic acid or ester thereof. Preferably, B is —COOR where R is H or lower alkyl such as methyl.

When the group B in compound (III) is hydroxy, it may be removed by chlorination and elimination, followed by hydrogenation. For example, chlorination and elimination may be effected by treatment with phosphorus oxychloride in the presence of triethylamine, or with thionyl chloride followed, where necessary, by DBN. The chloride or the unsaturated product may then be hydrogenated under conventional conditions, such as over 10% palladium/carbon in methanol. Alternatively, the compound (III) may be dehydroxylated by the use of thionyl chloride followed by treatment with tributyl tin hydride in a solvent such as tetrahydrofuran in the presence of a radical initiator such as azabisisobutyronitrile.

The compound of formula (III) where B is hydroxy may be prepared by reaction of a ketone compound of formula (IV) with a metal derivative of 2-chloropyrazine, of formula (V):

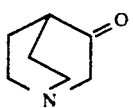 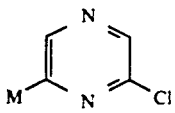

(IV)　　　(V)

wherein M represents a metal atom, for example lithium. The lithium derivative for instance may be prepared by reacting the corresponding iodo-substituted pyrazine (V) with t-butyl lithium.

When the group B in compound (III) is carboxy it may be removed by standard decarboxylation techniques such as heating in aqueous solution made to pH1 with hydrochloric acid.

The compounds of formula (III) where B represents a carboxy-containing group may be prepared by reaction of a compound of formula (VI) with a compound of formula (VII):

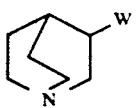 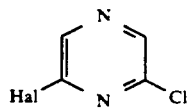

(VI)　　　(VII)

wherein Hal represents halo such as iodo, chloro or bromo; and W represents cyano, or a carboxylic acid group or a derivative thereof which activates the adjacent position, such as an alkyl ester; and subsequently, where necessary, converting the group W to a carboxy-containing group, preferably by hydrolysis.

Preferably, W represents an alkyl ester group such as methoxycarbonyl. Preferably, the halo group is chloro. The reaction between compounds (VI) and (VII) may be carried out in the presence of a strong base such as lithium diisopropylamide (which may be prepared in situ from n-butyl lithium and diisopropylamine) in a solvent such as tetrahydrofuran.

The 1-azabicyclo[2.2.2]octane moiety may be introduced into the molecules concerned by methods known from the art, in particular by methods analogous to those described in EP-A-239309 and EP-A-327155.

The separation of the enantiomers of the racemate corresponding to the compound (I) is preferably undertaken by optical resolution using (+)-di-O,O'-p-toluyl-D-tartaric acid; (−)-dibenzoyl-L-tartaric acid may also be used. The present invention therefore further provides a method for resolving the enantiomers of 3-[2-(6-chloropyrazin)yl]-1-azabicyclo[2.2.2]octane using a chiral acid resolution.

Alternatively, the substantially pure enantiomer of formula (I) may be prepared by cyclisation of a compound of formula (VIII) or a salt thereof:

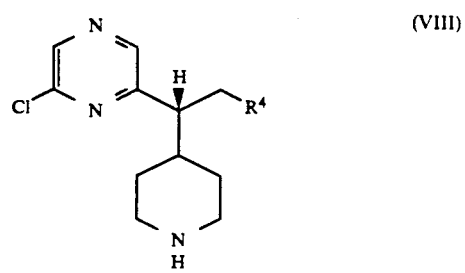

wherein $R^4$ is a labile leaving group such as mesylate ($OS(O)_2CH_3$) or halo such as chloro or bromo.

Cyclisation of (VIII) is carried out in a pH range of from 8 to 10, such as, preferably, in a two-phase system comprising a mild inorganic base such as an aqueous alkali or alkaline earth metal carbonate, hydrogencarbonate or hydroxide such as sodium or potassium carbonate or hydrogencarbonate or barium hydroxide; preferably aqueous potassium carbonate. The non-aqueous phase is any in which the compound of formula (I) so prepared is soluble, for example, solvents having a b.p. $\geq 60°$ C. such as a lower alkanol or ester such as t-butanol or ethylacetate, or an ether such as di-isopropyl ether, or toluene. For a single-phase system, any alcohol and water can be used, for example t-butanol/water. The compound of formula (VIII) is usually in a salt form such as the hydrochloride salt.

The following Examples illustrate the preparation and use of compound (I). In the Examples, all temperatures are in °C.; THF is tetrahydrofuran; and ether is diethyl ether.

DESCRIPTION 1

(a)

3-[2-(6-Chloropyrazin)yl]-3-carbomethoxy-1-azabicyclo[2.2.2]octane

A solution of lithium diisopropylamide in anhydrous THF was prepared by addition of n-butyllithium (6.66 ml of a 1.6M solution in hexane, 10.7 mmol) to a stirred solution of diisopropylamine (1.08 g, 10.7 mmol) in THF (30 ml), at −35° C. The solution was stirred for 0.5 h and then added dropwise to a solution of 3-carbomethoxy-1-azabicyclo[2.2.2]octane (1.5 g, 8.88 mmol) in THF (50 ml), at −78° C. The solution was stirred for 2 h before adding a solution of 2,6-dichloropyrazine (1.59 g, 10.7 mmol) in THF (15 ml), at −78° C. Stirring for 16 h at room temperature was followed by aqueous workup and extraction into dichloromethane. The crude product was chromatographed through silica-gel eluting with dichloromethane/methanol (92:8) to give the title-ester (1.51 g) as a yellow oil; (Found: $M^+ = 281.0920$; $C_{13}H_{16}N_3O_2Cl$ requires $M^+ = 281.09310$); δ (360 MHz, CDCl$_3$) 1.41-1.55 (2H, m, CH$_2$); 1.64-1.72 (2H, m, CH$_2$); 2.66-2.71 (1H, m, CH of CH$_2$N); 2.73-2.95 (4H, m, CH$_2$N, CH of CH$_2$N and CH-bridgehead); 3.64 (1H, dd, J=2.2 and 14.4 Hz, CH of CH$_2$N); 3.67 (3H, s, CO$_2$Me); 3.98 (1H, dd, J=2.2 and 14.4 Hz, CH of CH$_2$N); 8.47 (1H, s, pyrazine-H); 8.57 (1H, s, pyrazine-H).

(b) 3-[2-(6-Chloropyrazin)yl]-1-azabicyclo[2.2.2]octane. Hydrochloride

A solution of 3-[2-(6-chloropyrazin)yl]-3-carbomethoxy-1-azabicyclo[2.2.2]octane (1.0 g, 3.6 mmol) in concentrated (35%) hydrochloric acid (40 ml) was heated at 125° C. for 4 h. The solution was cooled to 10° C., dichloromethane (100 ml) added, and the aqueous basified to pH 10 with potassium carbonate, with stirring. The aqueous was separated and extracted with several portions of dichloromethane (4×50 ml). The residue remaining, after drying (Na$_2$SO$_4$) and removal of solvent, was chromatographed through alumina, eluting with dichloromethane/methanol (96:4) to give the title-chloropyrazine (0.25 g). The hydrochloride salt was prepared, m.p. 149°-151° C. (isopropyl alcohol/ether); (Found: C, 48.00; H, 5.79; N, 15.08. $C_{11}H_{14}N_3Cl.1.4HCl$ requires C, 48.09; H, 5.65; N, 15.29%); m/e 223 (M$^+$); δ (360 MHz, D$_2$O) 1.73-1.90 (2H, m, CH$_2$); 2.08-2.28 (2H, m, CH$_2$); 2.44-2.47 (1H, m, bridgehead-H); 3.29-3.38 (1H, m, CH of CH$_2$N); 3.42-3.56 (3H, m, CH$_2$N and CH of CH$_2$N); 3.62-3.69 (1H, m, CH of CH$_2$N); 3.77-3.82 (1H, m, CH of CH$_2$N); 4.01 (1H, dd, J=6.3 and 12.7 Hz, CH-pyrazine); 8.58 (1H, s, pyrazine-H); 8.59 (1H, s, pyrazine-H).

DESCRIPTION 2

(a)
3-[2-(6-Chloropyrazin)yl]-3-carbomethoxy-1-azabicyclo[2.2.2]octane

3-Carbomethoxy-1-azabicyclo[2.2.2]octane hydrochloride (1, 150 g, 0.73 mol) in H$_2$O (350 mL) was colled in an ice-bath, Na$_2$CO$_3$ (80 g, 0.76 mol) added and the mixture extracted with CH$_2$Cl$_2$ (5×300 mL). The combined organics were dried (Na$_2$SO$_4$) and evaporated and the residue in ether (500 mL) was filtered through a plug of cotton wool and then evaporated to give the free base as a colourless oil (110 g, 89%). n-Butyllithium (353 mL of a 1.6M solution in hexane, 0.57 mol) was added to a stirred solution of diisopropylamine (57.2 g, 0.57 mol) in anhydrous THF (800 mL), at −35° C. The solution was stirred for 0.5 h at −35° C. then cooled to −65° C. and a solution of 3-carbomethoxy-1-azabicyclo[2.2.2]octane (91.1 g, 0.54 mol) in THF (300 mL) added over a 0.75 h period. The resultant yellow solution was stirred for 1.5 h before adding a solution of 2,6-dichloropyrazine (84.2 g, 0.57 mol) in THF (300 mL) over a 0.66 h period at −65° C. The black reaction mixture was warmed to 0° C., stirred for 2 h, then quenched with water (600 mL). The mixture was extracted with CH$_2$Cl$_2$ (5×500 mL) and the material isolated from the organic extracts was purified by column chromatography on silica (Kieselgel 60, 0.04-0.063 mm, 1.0 Kg) eluting with CH$_2$Cl$_2$/MeOH (92:8). The title compound (a) was obtained as a pale yellow viscous oil which solidified on standing at 5° C.; R$_f$0.3 in CH$_2$Cl$_2$/MeOH (92:8) on silica plates; (Found: $M^+ = 281.0920$; $C_{13}H_{16}N_3O_2Cl$ requires $M^+ = 281.0931$); $^1$H NMR (360 MHz, CDCl$_3$) δ1.41-1.55 (2H, m, CH$_2$); 1.64-1.72 (2H, m, CH$_2$); 2.66-2.71 (1H, m, CH of CH$_2$N); 2.73-2.95 (4H, m, CH$_2$N, CH of CH$_2$N, and CH-bridgehead); 3.62 (1H, dd, J=2.2, 14.4 Hz, CH of CH$_2$N); 3.67 (3H, s, CO$_2$Me); 3.98 (1H, dd, J=2.2, 14.4 Hz, CH of CH$_2$N); 8.47 (1H, s, pyrazine-H) and 8.57 (1H, s, pyrazine-H).

(b) 3-[2-(6-Chloropyrazin)yl]-1-azabicyclo[2.2.2]octane

A solution of 3-[2-(6-chloropyrazin)yl]-3-carbomethoxy-1-azabicyclo[2.2.2]octane (101 g, 0.36 mol) in concentrated hydrochloric acid (600 mL) was heated at 130° for 3 h. The aqueous was concentrated (350 mL), cooled in an ice-bath and basified with solid K$_2$CO$_3$. The crude product was extracted into CH$_2$Cl$_2$ (5×500 mL), the combined extracts dried (Na$_2$SO$_4$) and evaporated. Column chromatography on neutral alumina (ICN Neutral Alumina, Grade 3, 750 g) using CH$_2$Cl$_2$/MeOH (98:2), followed by dissolving in ether (500 mL), filtration through a cotton wool plug and evaporation of solvent gave the title compound, (b), R$_f$0.3 in CH$_2$Cl$_2$/MeOH (98:2) on alumina plates. The compound was characterised as the hydrogen maleate salt, m.p. 114°-116° C.; (Found: C, 53.02; H, 5.35; N, 12.32. $C_{11}H_{14}N_3Cl.C_4H_4O_4$ requires C, 53.02; H, 5.34; N, 12.37%); MS, m/e 223 (M$^+$); $^1$H NMR (360 MHz, D$_2$O) δ 1.74-190 (2H, m, CH$_2$); 2.08-2.28 (2H, m, CH$_2$); 2.44-2.47 (1H, m, bridgehead-H); 3.28-3.37 (1H, m, CH of CH$_2$N); 3.40-3.55 (3H, m, CH$_2$N and CH of CH$_2$N); 3.61-3.68 (1H, m, CH of CH$_2$N); 3.76-3.80 (1H, m, CH of CH$_2$N); 4.01 (1H, dd, J=6.3, 12.7 Hz, CH-pyrazine); 6.29 (2H, s, maleate-H); 8.58 (1H, s, pyrazine-H) and 8.59 (1H, s, pyrazine-H).

EXAMPLE 1

(R)-3-[2-(6-Chloropyrazin)yl]-1-azabicyclo[2.2.2]octane hydrogen maleate

To a stirred solution of 3-[2-(6-chloropyrazin)yl]-1-azabicyclo[2.2.2]octane (7.4 g, 33.1 mmol) in ethanol (30 mL) was added a solution of (+)-d-O, O'-p-toluyl-D-tartaric acid (3.20 g, 8.28 mmol) in ethanol (25 mL), at room temperature. The DTT salt 6.56 g, 95% theoretical for one isomer) precipitated out almost immediately and was stirred for 1 h before filtering and washing with ethanol (50 mL) and then ether (30 mL). The DTT salt (6.50 g) was triturated with refluxing ethanol (100 mL) for 2 h, filtered whilst hot, washed with cold ethanol (30 mL) and dried under vacuum. The product (5.3 g) was determined to be 97.8% optically pure by chiral HPLC on a sample of the oxalate salt (see below). Trituration with hot ethanol (200 mL) a second time gave material (5.00 g) which was determined to be 99.6% optically pure. The ditoluyltartrate was taken up into 2-N K$_2$CO$_3$ solution (50 mL) and extracted with CH$_2$Cl$_2$ (4×75 mL). The combined extracts were dried (Na$_2$SO$_4$), evaporated, and the residue in ether (200 mL) filtered through a plug of cotton wool and the solvent evaporated to give the free base. To a solution of the free base (2.50 g, 11.2 mmol) in ether (50 mL) and methanol (5 mL) was added a solution of maleicacid (1 equivalent) in methanol. After ageing for 0.5 h at 5° C., the crude salt was collected (3.7 g) and recrystallised once from i-PA (20 mL) and ether (3 mL) to give the title compound as a white crystalline solid (3.3 g, 59%), m.p. 101°-103° C.; (Found: C, 53.00; H, 5.35; N, 12.32. $C_{11}H_{14}N_3Cl.C_4H_4O_4$ requires C, 53.02; H, 5.34; N, 12.37%); $R_f$ 0.3 in $CH_2Cl_2$/MeOH (98:2) on alumina plates; $[\alpha]_\Delta^{21} = -27.3°$ (c=1.0, $CH_2Cl_2$); $[\alpha]_\Delta^{21} = -20.4$ (c=1, MeOH); HPLC, chemical purity: $R_t$=10.43 min (99.9%) at g=280 nm on s Spherisorb RP-8 column (250×4.6 mm), 5 mm 10% MeCN in 50 mM $KH_2PO_4$, 0.2% TEA, pH=2.5 with $H_3PO_4$, flow rate (1 mL/min); enantiomeric purity: $R_t$=6.80 min (99.7%) at g 280 nm on a Chromtech Chiral AGP column, 10 mM $K_2HPO_4$, pH 6.2 with $H_3PO_4$, flow rate 0.6 ml/min; MS, m/e 223M+ of free base; $^1$H NMR (360 MHz, $D_2O$) γ 1.74-1.90 (2H, m, $CH_2$); 2.08-2.28 (2H, m, $CH_2$); 2.42-2.48 (1H, m, 4-CH); 3.28-3.37 (1H, m, CH of $CH_2N$); 3.40-3.55 (3H, m, $CH_2N$ and CH of $CH_2N$); 3.61-3.68 (1H, m, CH of $CH_2N$); 3.76-3.80 (1H, m, CH of $CH_2N$), 4.01 (1H, dd, J=6.3, 12.7 Hz, 3-CH); 6.29 (2H, s, maleate-H) and 8.56 (2H, s, pyrazine-H).

EXAMPLE 2

(R)-3-[2-(6-Chloropyrazin)yl]-1-azabicyclo[2.2.2]octane Sesquioxalate

The title compound free base was obtained by the optical resolution of 3-[2-(6-chloropyrazin)yl]-1-azabicyclo[2.2.2]octane using (−)-O,O'-dibenzoyl-L-tartaric acid. To a solution of (R)-3-[2-(6-chloropyrazin-)yl]-1-azabicyclo[2.2.2]octane (79.2 mg, 0.35 mmol) in methanol/diethyl ether was added a solution of oxalic acid (35.1 mg, 1.1 equivalents) in diethyl ether. The salt was collected then recrystallised from methanol/-diethyl ether, m.p. 173°-177° C. (Found: C, 47.02; H, 4.82; N, 11.76. $C_{11}H_{14}N_3Cl$. 1.5 $C_2H_2O_4$ requires C, 46.87; H, 4.78; N, 11.71%). $[\alpha]_D = +12°$ (c=0.35, water).

PHARMACEUTICAL EXAMPLES

1. Tablets containing 1-25 mg of compound (1)

|  | Amount-mg | | |
|---|---|---|---|
| Compound (1) | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

2. Tablets containing 26-100 mg of compound (1)

|  | Amount-mg | | |
|---|---|---|---|
| Compound (1) | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

Compound (1), lactose, and a portion of the corn starch are mixed together and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100.0 mg of compound (1) per tablet.

BIOLOGICAL ACTIVITY

The following results are obtained in pharmacological assays to allow agonist activity against muscarinic receptors in the ganglion, heart and ileum.

| Compound | Ganglion ($EC_{50}$) (μM) | Heart ($pA_2$) | Ileum ($EC_{50}$) (μM) |
|---|---|---|---|
| (1):(R) isomer Comparative data for corresponding | 0.05 | 7.2 | 0.04 |
| (S) isomer | 0.20 | 6.9 | 0.60 |
| racemate | 0.10 | 7.1 | 0.03 |

EXAMPLE 3

(R)-(−)-3-(6-Chloropyrazin-2-yl)-1-azabicyclo [2.2.2] octane hydrogen tartrate

A. Preparation of N-tert-butoxycarbonyl piperidin-4-one (13)

To a stirred slurry of sodium bicarbonate (476 g) in water (545 ml) at room temperature was added a solution of 4-piperidinone monohydrochloride monohydrate (12, ex Lancaster Synthesis, 727 g, 4.73 mol) in water (2.47 l) over 20 minutes. To the resultant thin slurry was added di-tert-butyldicarbonate (1.05 kg) in portions over 30 minutes (gas evolution - but no exotherm and little frothing). The mixture was warmed to 35° C. over 1 hour, aged for 1 hour, then warmed to 50° C. and held for 2.5 hours.

The mixture was allowed to stir at 50° C. for a further 30 minutes, cooled to ~30° C. and ethyl acetate (700 ml) added. The aqueous layer was separated, re-extracted with ethyl acetate (300 ml) and the organic extracts combined. The organic solution was washed with saturated brine solution (300 ml) and then evaporated (Büchi) to yield the product as a colourless solid. The solid was dried in vacuo at room temperature overnight to give the product as a colourless solid, m.p. 74°-5° C.

B. Preparation of Ethyl-2-[(N-tert-butoxycarbonyl piperidin)-4-ylidene]acetate(14).

Triethylphosphonoacetate (1.42 kg, 6.35 mole) was added to a stirred slurry of milled anhydrous potassium carbonate (2.02 kg, 14.66 mole) in DMF (9.7 l). The piperidinone (13, ex. step 3A) was added in one portion.

The resultant mixture was stirred and heated under $N_2$ atmosphere at 70° C.+1° C. for 22 hours in total. Water (30 l) was added dropwise to the cooled reaction mixture (T=30°→35° C.). The slurry was aged at 0°-5° C. overnight. The slurry was filtered, the product washed with water (6 l) and dried at room temperature in vacuo overnight. The product was obtained as a colourless solid, m.p. 84.5°-85.5° C.

C. Preparation of Ethyl-2-[(N-tert-butoxycarbonyl piperidin)-4-yl] acetate (15)

To a stirred slurry of unsaturated ester (14, 1.285 kg, 4.77 mole, ex step 3B) in IMS (12.8 l) at 18° C. under $N_2$ was added a slurry of 10% Pd/C(128 g) in water (400 ml). 10M Ammonium formate solution (930 ml) was added dropwise over 30 minutes. On complete addition, the mixture was stirred for a further 30 minutes. (N.B. slight exotherm noted over ~40 mins, from 18°→24° C.). After 1 hour GC showed complete reaction. The reaction was filtered through HYFLO which was then washed with IMS (3 1). The filtrate and washings were combined and evaporated to residue. The residue was partitioned between hexane (500 ml) and water (1 l). The organic layer was separated, washed with water ($2\times500$ ml) and evaporated to yield a colourless mobile oil which crystallised on standing. The ester (15), was obtained as a colourless solid, m.p. 31° C.

D. Preparation of Ethyl-2-[(N-tert-butoxycarbonyl piperidin)-4-yl]-2-(6-chloropyrazin-2-yl) acetate (16)

To a stirred solution of 1M sodium bis(trimethylsilyl) amide in THF (1.66 l, 1.66 mole) at $-28°$ C. under $N_2$ atmosphere was added a solution of 2,6-dichloropyrazine (115.5 g, 0.77 mole) and ester (15, ex step 3C, 200 g, 0.74 mole) in THF (400 ml) dropwise over ~20 minutes maintaining reaction temperature at $-20°\rightarrow-15°$ C. On complete addition the reaction was stirred at $-10°$ C. for 30 minutes. Hexane (400 ml) was added at $-10°$ C. followed by the dropwise addition of 2M hydrochloric acid (1 l). The lower aqueous phase was separated and the organic phase washed with 2M hydrochloric acid (500 ml) and saturated brine ($2\times500$ ml), dried ($MgSO_4$) and evaporated to give the crude product as a dark oil.

E. Preparation and resolution of 2-[(N-tertbutoxycarbonylpiperidin)-4-yl]-2-(6-chloropyrazin-2-yl)acetic acid (17)

A solution of sodium hydroxide pellets (46 g, 1.15 mole) in water (1.6 l) was added to a solution of crude racemic ester (16, ex step 3D, 320 g, 0.738 mole) in IMS (1.6 l) at room temperature. The dark solution was stirred for 1 hour (N.B. small exotherm$\rightarrow$30° C.). After a further 30 minutes at room temperature, HPLC showed complete reaction. The bulk of the IMS was removed in vacuo, T<40° C. (Büchi) and the aqueous residue was extracted with ethyl acetate ($3\times500$ ml). The aqueous solution was acidified with concentrated hydrochloric acid (100 ml) and extracted with ethyl acetate ($2\times500$ ml). The organic extracts were combined, washed with brine (300 ml), dried ($MgSO_4$) and evaporated to give crude racemic acid (17) as a gum which solidified on standing. This crude acid (275 g) was dissolved in ethyl acetate (2.0 l) at room temperature and a solution of (L)-(−)-A-methylbenzylamine (56 g, 0.46 mole) in ethyl acetate (200 ml) added dropwise over ~20 minutes. The resulting slurry was aged at 25° C. for 30 minutes, at 50° C. for 1 hour and then cooled to room temperature, held for 1 hour and then filtered. The acid salt was washed with ethyl acetate (300 ml) and dried in vacuo at room temperature overnight to give partially resolved (+)-acid salt (17) as a white, cyrstalline solid, $[Á]D,20= +7.8$ (c=0.25, $CH_2Cl_2$). The above salt (180 g) was swished in ethyl acetate (1.8 l) at gentle reflux for 1 hour, cooled to room temperature, aged for 1 hour and filtered. The cake was washed with ethyl acetate (300 ml) and dried in vacuo overnight, $[Á]D,20= +12.5°$. This swish was repeated to give $[Á]D,20= +12.8°$(c=0.25, $CH_2Cl_2$). [Susequent investigation has shown that an optical rotation of 13.8° is achievable. Hence +12.8° is equivalent to 95.7% major isomer.]

Racemisation of Acid (17)—General Procedure

Trimethylsilylchloride (1.3 equivs.) was added dropwise to a stirred solution of enantiomerically enriched acid (17, 1 equiv.) and triethylamine (3 equivs.) in ethyl acetate (10 mlg-1 relative to acid (17)) at room temperature maintaining temperature at 20°-30° C. under $N_2$ atmosphere. The resulting slurry was stirred at room temperature for a further 15 minutes and then heated under gentle reflux for 7.5 hours. The reaction mixture was cooled to room temperature and washed with 2M aqueous hydrochloric acid ($-4$ mlg$^{-1}$) relative to acid (17) and (1 mlg$^{-1}$) then saturated brine ($2\times2$ mlg-l), dried ($MgSO_4$) and evaporated to give racemic acid (17) in quantitive recovery.

F. Preparation of (S)-(+)-2-[(N-tert-Butoxycarbonyl piperidin)-4-yl]-2-(6-chloropyrazin-2-yl) ethanol (18)

Resolved (+)-acid salt (17, ex step 3E, 30 g, 63 mmole) was partitioned between ethyl acetate (100 ml) and 1M hydrochloric acid (100 ml). The lower aqueous layer was separated and extracted with ethyl acetate (25 ml). The organic extracts were combined, washed with saturated brine solution ($2\times50$ ml), and evaporated to give resolved acid (17, 22.3 g) as a crystalline solid in 100% recovery. The acid (22.3 g) was dissolved in anhydrous THF (67 ml) and cooled to $-20°$ C., under $N_2$ atmosphere with stirring. 1M borane in THF (Aldrich, 189 ml, 3 equivs.) was added dropwise maintaining temperature at $-20°$ C. $\rightarrow-15°$ C. The resulting solution was stirred at 0° C. for 1 hour and then allowed to warm to room temperature. After a further 2.5 hours, the reaction was complete and was cooled to 0° C. Water (100 ml) was added (carefully) and the mixture stirred vigorously at room temperature until hydrolysis was complete (LC). The THF was evaporated (Büchi) and the aqueous residue extracted with ethyl acetate ($3\times80$ ml). The organic extracts were combined, washed with saturated brine solution (80 ml) and evaporated to give an oil. The oil was preabsorbed on silica (50 g), placed on top of clean silica (50 g) in a filter funnel and eluted with 1:1, EtOAc:hexane ($6\times200$ ml). Evaporation of the product containing fractions gave alcohol (18) as a viscous oil. $[Á]D,20= +50.8°$ (c=1.2 in MeOH).

G. Preparation of (S)-(+)-2-[(N-tert-Butoxycarbonyl piperidin)-4-yl]-2-(6-chloropyrazin-2-yl) ethanol methanesulphonate ester (19)

Triethylamine (16.2 ml, 116 mmole) was added to a stirred solution of the alcohol (18, 13.1 g, 38.4 mmole, ex step 3F in ethyl acetate (130 ml) at $-20°$ C. under $N_2$ atmosphere. Methanesulphonyl chloride (4.2 ml) was then added dropwise maintaining reaction temperature at $-15°$ C. $\rightarrow-20°$ C. The slurry was stirred at $-15°$ C. for 30 minutes when 1M hydrochloric acid (100 ml) was added maintaining temperature <0° C. The lower aqueous layer was separated and the organic layer washed with 1M hydrochloric acid (50 ml), 50% aqueous saturated brine solution ($2\times50$ ml), dried ($MgSO_4$) and evaporated to give mesylate (19) as a pale yellow foam. $[Á]D, 20= +22.6°$ (c=1, MeOH).

H. Preparation of (R)-(−)-3-(6-chloropyrazin-2-yl)-1-azabicyclo[2.2.2]octane hydrogen tartrate The crude mesylate (19, 15.9 g, 37.9 mmole, ex step 3G) was dissolved in ethyl acetate (160 ml). Dry hydrogen gas was bubbled through the solution with mechanical stirring at 15°-20° C. The deprotection was followed by TLC (Ether/Silica), and was complete after ~2 hours. Water (60 ml) was added to the resulting thick slurry followed by the careful addition of 1:1 wt/wt potassium carbonate/water (80 ml). On complete addition (pH>9) the two phase mixture was heated to 60° C. with stirring. The cyclisation was followed by HPLC.

After 4 hours at 60° C., the reaction mixture was cooled to 25° C. and the lower aqueous layer was extracted with ethyl acetate (2×50 ml) and the organic extracts combined, washed with brine (50 ml) and dried (MgSO$_4$). Evaporation of the solvent gave crude free base as a pale yellow oil. The oil (7.7 g) was dissolved in 1:1 IPA/ethyl acetate (50 ml) and added to a warm (50° C.) solution of L-tartaric acid in 1:1 IPA/ethyl acetate (100 ml). The resultant slurry was allowed to cool to room temperature with stirring overnight. The slurry was aged at 0°-5° C. for 1 hour, filtered, washed with 1:2, IPA/ethyl acetate (30 ml) and dried in vacuo at room temperature to give tartrate salt as a white, crystalline solid. The salt (9.4 g) was dissolved in methanol (282 ml) at gentle reflux. The solution was cooled slightly and filtered hot. The filter paper was rinsed with methanol (30 ml). The solution was concentrated in vacuo at −35° C. to a volume of −100 ml. The resulting slurry was aged at room temperature for 30 minutes, then at 0°-5° C. for 1 hour, filtered and washed with cold methanol (20 ml). The semi-purified salt was dried in vacuo at room temperature. The salt was upgraded by swishing in prefiltered refluxing methanol (10 mlg$^{-1}$) for 1 hour. The slurry was cooled to room temperature, held for 1 hour, filtered, washed with methanol and dried in vacuo to give pure tartrate salt, m.p. 175°-6° C., [α]20,405= +62.6°; [α]20,589= +24.5° (c=1, H$_2$O).

| HPLC Profile | @ λ 279 nm | r.r.t. | Area % |
|---|---|---|---|
| | | 0.61 | <0.1 |
| | | 1.00 | 99.8 |
| | | 1.44 | <0.2 |
| | @ λ 209 nm | 0.62 | −0.1 |
| | | 1.00 | 99.6 |

We claim:

1. A compound selected from (R)-3-[2-(6-chloropyrazin)yl]-1-azabicyclo[2.2.2]octane and salts thereof.

2. A salt according to claim 1 selected from the group consisting of hydrochloride, hydrogen maleate and hydrogen tartrate salts of the compound.

3. A pharmaceutical composition comprising a compound selected from (R)-3-[2-(6-chloropyrazin)yl]-1-azabicyclo[2.2.2]octane and pharmaceutically acceptable salts thereof and a pharmaceutically acceptable carrier therefor.

4. A process for preparing a composition according to claim 3 which process comprises bringing a compound selected from (R)-3-[2-(6-chloropyrazin)yl]-1-azabicyclo[2.2.2]octane and pharmaceutically acceptable salts thereof into association with a pharmaceutically acceptable carrier therefor.

5. A method for the treatment or prevention of neurological and mental disorders which method comprises administering to a patient in need thereof a therapeutically effective amount of a compound selected from (R)-3-[2-(6-chloropyrazin)yl]-1-azabicyclo[2.2.2]-octane and pharmaceutically acceptable salts thereof.

6. A method according to claim 5 wherein the disorder is dementia.

* * * * *